United States Patent [19]
Belyavsky et al.

[11] Patent Number: 6,120,996
[45] Date of Patent: *Sep. 19, 2000

[54] METHOD OF IDENTIFICATION AND CLONING DIFFERENTIALLY EXPRESSED MESSENGER RNAS

[75] Inventors: Alexander V. Belyavsky; Natalia B. Ivanova, both of Moscow, Russian Federation

[73] Assignee: New York Blood Center, Inc., New York, N.Y.

[ * ] Notice: This patent is subject to a terminal disclaimer.

[21] Appl. No.: 08/964,143

[22] Filed: Nov. 6, 1997

Related U.S. Application Data

[63] Continuation of application No. 08/499,899, Jul. 11, 1995, Pat. No. 5,814,445.

[30] Foreign Application Priority Data

Jul. 11, 1994 [RU] Russian Federation ............. 94024056

[51] Int. Cl.[7] .............................. C12Q 1/68; C12P 19/34; C07H 21/02; C07H 21/04
[52] U.S. Cl. .......................... 435/6; 435/91.2; 435/91.51; 536/24.2; 536/24.33
[58] Field of Search .......................... 435/6, 91.2, 91.51; 536/24.33, 24.2; 935/77, 78, 8

[56] References Cited

U.S. PATENT DOCUMENTS

| | | | |
|---|---|---|---|
| 5,213,961 | 5/1993 | Bunn et al. | 435/6 |
| 5,382,511 | 1/1995 | Stapleton | 435/6 |
| 5,459,037 | 10/1995 | Sutcliffe et al. | 435/6 |
| 5,525,486 | 6/1996 | Honjo et al. | 435/69.1 |
| 5,580,726 | 12/1996 | Villeponteau et al. | 435/6 |
| 5,599,672 | 2/1997 | Liang et al. | 435/6 |
| 5,599,696 | 2/1997 | Mueller et al. | 435/91.2 |
| 5,618,702 | 4/1997 | Scanlon | 435/91.2 |
| 5,643,730 | 7/1997 | Banker et al. | 435/6 |
| 5,643,765 | 7/1997 | Willey | 435/91.2 |
| 5,643,766 | 7/1997 | Scheele et al. | 435/912 |
| 5,656,462 | 8/1997 | Keller et al. | 435/91.2 |
| 5,665,544 | 9/1997 | Chenchik et al. | 435/6 |
| 5,665,547 | 9/1997 | Pardee et al. | 435/6 |
| 5,712,126 | 1/1998 | Weissman et al. | 435/91.2 |
| 5,716,785 | 2/1998 | Van Gelder et al. | 435/6 |
| 5,804,383 | 9/1998 | Gruenert et al. | 435/6 |

FOREIGN PATENT DOCUMENTS

| | | |
|---|---|---|
| 0 356 021 | 2/1990 | European Pat. Off. . |
| 0 534 858 | 3/1993 | European Pat. Off. . |
| WO 89/10977 | 11/1989 | WIPO . |
| 90/01065 | 2/1990 | WIPO . |
| WO 90/01065 | 2/1990 | WIPO . |
| WO 91/18114 | 11/1991 | WIPO . |
| WO 95/13369 | 5/1995 | WIPO . |
| WO 97/17466 | 5/1997 | WIPO . |

OTHER PUBLICATIONS

Shahan et al., "Tissue Specific Expression of Major Urinary Protein (MUP) Genes in Mice: Characterization of MUP mRNAs by Restriction Mapping of cDNA and by In Vitro Translation," Molecular and Cellular Biology, Nov. 1984, vol. 4, No. 11, p. 2259–2265.

Kimmel et al., in *Methods in Enzymology,* vol:152 (Berger et al., eds), 1987, pp. 307–316, Academic Press, Inc., San Diego, CA.

Chang et al., "T200 Alternate Exon Use in Murine Lymphoid Cells Determined by Reverse Transcription–Polymerase Chain Reaction", Journal of Immunology, Jul. 1989, vol. 143, p. 315–321.

Brenner et al., "Message Amplification Phenotyping (MAPping): A Technique to Simultaneously Measure Multiple mRNAs from Small Numbers of Cells," *BioTechniques,* vol. 7, No. 10 (1989), pp. 1096–1103.

Buck et al., "A Novel Multigene Family May Encode Odorant Receptors: A Molecular Basis for Odor Recognition," *Cell,* vol. 65, 175–187, Apr. 5, 1991.

de Kant et al., "Gene Expression Analysis by a Competitive and Differential PCR with Antisense Competitors," *BioTechniques,* vol. 17, No. 5, 1994, pp. 934–942.

Dougherty et al., "Restriction Endonuclease Digestion Eliminates Product Contamination in Reverse Transcribed Polymerase Chain Reaction," *J. Virol Methods,* Feb. 1993, vol. 41, No. 2, pp. 235–238.

Erlander et al., "PCR–Based Technologies to Study Differential Gene Expression in Rat Brain," *Proceedings of the third International Workshop on the Identification of Transcribed Sequences, held Oct. 2–4, 1993, in New Orleans, Louisiana,* pp. 261–271.

Frohman et al., "Rapid Production of Full–Length cDNAs from Rare Transcripts: Amplification Using a Single Gene–Specific Oligonucleotide Primer," *Proc. Natl. Acad. Sci.,* vol. 85, pp. 8998–9002. Dec. 1988.

Heidmann et al., "Identification of Pre–mRNA Polyadenylation Sites in *Saccharomyces cerevisiae,*" Molecular and Cellular Biology, vol. 12, No. 9, Sep. 1992, pp. 4215–4229.

(List continued on next page.)

*Primary Examiner*—Jeffrey Fredman
*Attorney, Agent, or Firm*—Morgan, Lewis & Bockius LLP

[57] ABSTRACT

A method of identification of differentially expressed messenger RNA (mRNA) which consists of synthesizing from a set of sequences of mRNA sets of fragments of complementary DNA (cDNA), which are separated with the aid of gel electrophoresis and the pictures of separation of the cDNA from different types of cells are compared and fragments with differential signal intensity are identified. For formation of the set of fragments the cDNA is cleaved with the aid of restriction nucleases. A method of cloning of differentially expressed mRNAs consists of synthesizing from sets of sequences of mRNAs from different types of cells sets of fragments of complementary DNA (cDNA) which are separated with the aid of gel electrophoresis, the pictures of the separation of the cDNA from different types of cells are compared, fragments of cDNA with different signal intensities are separated from the gel, amplified with the aid of a polymerase chain reaction and cloned to a plasmid or phage vector. For the formation of the set of fragments one carries out cleavage of the cDNA with the aid of restriction endonucleases and uses only those fragments of cDNA that correspond to the 3' or 5' end regions of the mRNAs.

29 Claims, 6 Drawing Sheets

OTHER PUBLICATIONS

Ivanova et al., "Novel Method of Comparative Gene Expression Analysis and Identification of Differentially Expressed mRNAs," *Molecular Biology*, vol. 28, No. 6, Pt. 2, pp. 848–853, 1995.

Ralph et al., "RNA Fingerprinting Using Arbitrarily Primed PCR Identifies Differentially Regulated RNAs in Mink Lung (My1Lu) Cells Growth Arrested by Transforming Growth Factor β1," *Proc. Natl. Acad. Sci.*, vol. 90, pp. 10710–10714, Nov. 1993.

Wilson et al., "Nucleotide Sequence of 3' Untranslated Portion of Human Alpha Globin mRNA," *Nucleic Acids Research*, vol. 4, No. 7, Jul. 1977, pp. 2363–2368.

Yokoi et al., "A 3' Splice Site Consensus Sequence Mutation in the Intron 3 of the α–Galactosidase A Gene in a Patent With Fabry Disease," *Jpn. J. Human Genet.*, vol. 36, pp. 245–250, 1991.

Zhang et al, "Molecular Cloning and Expression of Murine Thromboxane Synthase," *Biochemical and Biophysical Research Communications*, vol. 194, No. 2, Jul. 30, 1993; pp. 741–748.

Bachem, Christian W.B., et al., Visualization of differential gene expression using a novel method of RNA fingerprinting based on AFLP: Analysis of gene expression during potato tuber development, *The Plant Journal*, (1996) 9 (5), pps. 745–753.

Coleclough, Christopher, et al., Use of primer–restriction–end adapters in a novel cDNA cloning strategy, *Gene*, 34 (1985) pps. 305–314.

Isegawa, Yuji, et al., Selective amplification of cDNA sequence from total RNA by cassette–ligation mediated polymerase chain reaction (PCR):Application to sequencing 6•5 kb genome segment of hantavirus strain B–1; *Molecular and Cellular Probes* (1992) 6, pps. 467–475.

Kurtz, David T., et al., Cloning of $\alpha_{2u}$ globin cDNA using a high efficiency technique for the cloning of trace messenger RNAs, *Gene*, 13 (1981).

Monstein, Hans–Juerg, et al., Structure and expression in protochordates resemble that of procholecystokinin in mammals; *Federation of European Biochmical Societies,* (1993) vol. 331, No. 1,2, 60–64.

Ni, et al., *Molecular Cloning of DNA;* pp. 398–399, Undated.

Okayama, Hiroto, et al., "High–Efficiency Cloning of Full–Length cDNA," *Molecular and Cellular Biology,* Feb. 1982, vol. 2, No. 2, pps.161–170.

Reddy, P. Gopal, et al., "Identification and Cloning of Genes Involved in Progression of Transformed Phenotype," *Methods in Molecular Genetics*, vol. 1, pps. 68–101, Undated.

Roux, Kenneth H., et al., "A Strategy for Single Site PCR Amplification of dsDNA: Priming Digested Cloned or Genomic DNA from an Anchor–Modified Restriction Site and a Short Internal Sequence," *BioTechniques,* vol. 8, No. 1 (1990), pps. 48–57.

Shyamala, Venkatakrishna, et al., Genome walking by single–specific–primer polymerase chain reaction: SSP–PCR*, *Gene* 84 (1989), pps. 1–8.

Uematsu, Yasushi, et al., "The T–cell–receptor repertoire in the synovial fluid of a patient with rheumatoid arthritis is polyclonal," *Proc. Natl. Acad. Sci. USA,* (Oct. 1991), vol. 88, pps. 8534–8538.

Wood et al., "Gel Electrophoresis of Nucleic Acids: A Practical Approach", Oxford University Press, (1990).

Lee et al., "Reusable cDNA Libraries Coupled to Magnetic Beads", Analytical Biochemistry, No. 206, (1992) pp. 206–207.

Ko, "An Equalized cDNA Library by the Reassociation of Short Double–Stranded cDNAs", Nucleic Acids Research, vol. 18, No. 19, (1990) pp. 5705–5711.

"Progmega Protocols and Applications Guide: Restriction Enzymes and Linkers", Promega Protocols and Applications Guide, (1991) pp. 1–43.

"Short Protocols in Molecular Biology: A Compendium of Methods from Current Protocols in Molecular Biology", (1989) pp. 75–76 Ausubel et al.

Siebert et al., "A New Method for Amplification of 5'–cDNA Ends" Clontechniques: Innovative Tools Molecular Biology, vol. VIII, No. 1 (1993) pp. 1–3.

Molecular Biology/Reagent Systems, Promega.

Welsh et al., "Arbitrarily Primed PCR Fingerprinting of RNA", Nucleic Acids Research, vol. 20, No. 19, (1992) pp. 4965–4970.

Ralph et al., "RNA Fingerprinting Using Arbitrarily Primed PCR Identifies Differentially Regulated RNAs in Mink Lung (My1Lu) Cells Growth Arrested by Transforming Growth Factor B1" Proc. Natl. Acad. Sci.

Liang et al., "Differential Display of Eukaryotic Messenger RNA by Means of the Polymerase Chain Reaction", Science, vol. 257, (1992) pp. 967–971.

Liang et al., "Distribution and Cloning of Eukaryotic mRNAs by Means of Differential Display: Refinements and Optimization", Nucleic Acids Research, vol. 21, No. 14, (1993) pp. 3269–3275.

Bauer et al., Identification of Differentially Expressed mRNA Species by an Improved Display Technique (DDRT–PCR), Nucleic Acids Research, vol. 21, No. 18, (1993) pp. 4272–4280.

Sargent, "Isolation of Differentially Expressed Genes", Methods in Enzymology, vol. 152, (1987) pp. 423–433.

Debuire et al., "Nonisotopic Competitive RT–PCR Assay to Measure MDR1 Gene Expression", Clin. Chem. vol. 41, No. 6, (1995) pp. 819–825.

Skolov et al., "A Rapid and Simple PCR–Based Method for Isolation of cDNAs From Differentially Expressed Genes", Nucleic Acids Research, vol. 22, No. 19, (1994) pp. 4009–4015.

FIG-4A

| 1 | 2 | 3 |

| 1 | 2 | 3 |

— 2036bp
— 1636bp
— 1018bp
— 506bp
— 396bp
— 344bp

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
       (A) LENGTH: 22 nucleotides
       (B) TYPE: nucleic acid
       (C) STRANDEDNESS: single
       (D) TOPOLOGY: linear (xi) SEQUENCE DESCRIPTION: SEQ ID NO:1:

GGGAGGCCCT TTTTTTTTTT TT                      22

(2) INFORMATION FOR SEQ ID NO:2:

(i) SEQUENCE CHARACTERISTICS:
       (A) LENGTH: 21 nucleotides
       (B) TYPE: nucleic acid
       (C) STRANDEDNESS: single
       (D) TOPOLOGY: linear (xi) SEQUENCE DESCRIPTION: SEQ ID NO:2:

AAGGAATTCC CCCCCCCCCC C                       21

(2) INFORMATION FOR SEQ ID NO:3:

(i) SEQUENCE CHARACTERISTICS:
       (A) LENGTH: 27 nucleotides
       (B) TYPE: nucleic acid
       (C) STRANDEDNESS: single
       (D) TOPOLOGY: linear (xi) SEQUENCE DESCRIPTION: SEQ ID NO:3:

GATCGTTTTT TGAAGCTTGG AGCCCAC                 27

(2) INFORMATION FOR SEQ ID NO:4:

(i) SEQUENCE CHARACTERISTICS:
       (A) LENGTH: 23 nucleotides
       (B) TYPE: nucleic acid
       (C) STRANDEDNESS: single
       (D) TOPOLOGY: linear (xi) SEQUENCE DESCRIPTION: SEQ ID NO:4:

GTGGGCTCCA AGCTTCAAAA AAC                    23

(2) INFORMATION FOR SEQ ID NO:5:

(i) SEQUENCE CHARACTERISTICS:
       (A) LENGTH: 16 nucleotides
       (B) TYPE: nucleic acid
       (C) STRANDEDNESS: single
       (D) TOPOLOGY: linear (xi) SEQUENCE DESCRIPTION: SEQ ID NO:5:

GTGGGCTCCA AGCTTC                           16

METHOD OF IDENTIFICATION AND CLONING DIFFERENTIALLY EXPRESSED MESSENGER RNAS

This application is a continuation of application Ser. No. 08/499,899, filed on Jul. 11, 1995, now U.S. Pat. No. 5,814,415.

ART

This invention relates to the field of molecular biology and can be used in medicine and molecular biology for analysis of gene expression and diagnosis and identification of mechanisms of pathology at the genetic level.

PRIOR ART

Differential expression of genes, which is realized via the synthesis of various sets of messenger RNAs (mRNAs), is the basis of the variety of phenotypes and functions of the cells of living organisms. In this connection one can understand the importance of methods that might allow identification and investigation of differentially expressed mRNAs, i.e., those RNAs, whose concentration in the cellular mRNA pool differs in two or more types of cells or changes in dependence on the functional state of the cells.

A number of methods have been described for the detection and cloning of differentially expressed mRNAs. In most cases they come down to the use of the method of hybridization of nucleic acids. In the differential screening method (see literature [1]) by means of transfer to nitrocellulose or nylon filters replicas of libraries of complementary DNA (cDNA) from the population of cells A sown in dishes are hybridized alternately with labeled preparations of cDNA from the population of cells A, B, C and so forth. Since the hybridization signal obtained from individual clones theoretically should be proportional to the representation of the corresponding cloned sequence in the cDNA preparation, one can, from the level of the signal obtained from different preparations, identify clones corresponding to genes that are expressed differentially in the populations of cells A, B and so forth. An important shortcoming of this approach is its low sensitivity, since only highly represented sequences (as a rule, those comprising at least 0.1% mRNA) can be detected. For less common sequences the hybridization signal does not exceed the background. In addition, in this approach one can examine only a small number (from several thousands to several tens of thousands) of clones. Another shortcoming is that information about the individuality of the clone (the description of its location in the dish or replica) is lost at the end of work with these replicas and cannot be used in subsequent experiments. Moreover, cDNA libraries from different types of cells are not comparable in that identical sequences occupy different places on filters in different libraries. Thus, conversion from one type of cells to other types is essentially impossible. Recently attempts have been made to create ordered cDNA libraries containing individual clones distributed in the cells of 96-well planchets. However, this does not eliminate the principal shortcoming of low sensitivity. In addition, sets of clones obtained from one type of cell are still not comparable to sets of clones from another type of cell.

The method of subtracted hybridization is used in order to overcome the low sensitivity of the differential screening method [1]; in this method a cDNA preparation from cells A is hybridized with a cDNA or mRNA preparation from cells B, after which the resulting hybrids are removed by one or another method. The resulting preparation is rich in sequences that are specific for preparation A. This "subtracted" preparation can be used both for the creation of libraries and for differential screening, since it makes it possible both to increase the probability of finding differentially expressed sequences and to increase the sensitivity of detection of poorly represented sequences. However, the use of this procedure makes the approach lengthy and laborious and, in addition, the gain in sensitivity is still insufficient for detection of rare sequences and is accompanied by the loss of the possibility of making a direct comparison of the level of gene expression in different cells.

Recently a modification of the differential screening method was proposed, in which instead of cloned sequences large orderly arranged sets of oligonucleotides are used for immobilization on a solid substrate, for example, all possible tetradecanenucleotides containing the common sequence AATAAA, which is encountered in most mRNAs [2]. This method theoretically provides an exhaustive search of a much larger set of mRNA sequences than in standard differential screening. The shortcoming of this approach, like other differential screening methods, is that under conditions of hybridization with an excessively complex mixture of cDNA molecules, the frequencies of representation of which may vary by factors of hundreds and thousands, the probability of the appearance of false signals owing to cross hybridization becomes significant, which makes reliable detection and quantitative analysis of rare mRNA sequences problematical. An additional problem is the need for synthesis and immobilization on a small area of from several dozens to hundreds of thousands of oligonucleotides, which requires a large initial investment. In addition, the approach in and of itself does not provide the possibility of cloning any long segments of differentially expressed mRNAs, which requires a separate operation.

Closest to the present invention is a method which is called "PCR mated with reverse transcription, with arbitrary primers" (arbitrary primed RT-PCR). In this method cDNA synthesized by mRNA is used to create a set of cDNA fragments of discrete length with the aid of a polymerase chain reaction (PCR) using primers of a random sequence under nonrigorous conditions which contribute to priming and amplification not of one, as is usual in standard PCR, but rather of a whole group of cDNA sequences. The set of discrete cDNA fragments is separated by electrophoresis in acrylamide gel and compared with a set of fragments obtained under identical conditions from a different type of cell. By using many arbitrary primers, one can compare one or several discrete cDNA fragments to most mRNA species. Two principal modifications of this approach have been proposed. One of them uses one or two "arbitrary" primers [3, 4]. The second approach uses one arbitrary and one oligo(dT) primer that contains two additional bases at the 3' end [5, 6, 7]. In this case the amplified segments are adjacent to the 3' end (poly(A) tail) of the mRNA. An important shortcoming of this approach is the fact that no more than a few dozen sequences are amplified in a single reaction. Thus, for an exhaustive search of 10–15 thousand RNA sequences expressed in individual types of cells or tissues, as a minimum several hundred (probably several thousand) reactions must be carried out. In addition, the sampling of sequences amplified in one reaction is random and, therefore, in the exhaustive search of a significant portion of sequences of cellular mRNA there will be a very significant accumulation of excess information. Thus, after a survey of 50% of all sequences, in each subsequent reaction only ½ of the amplified sequences will be new. At a depth of review of 90% the fraction of new sequences will fall to ¹⁄₁₀. Probably the most significant shortcoming of the approach is its poor reproducibility, which is connected with the fact that under weakly selective priming conditions small variations in the starting conditions or the quality of the RNA preparations, primers and other parameters will cause significant quantitative changes in the spectrum of amplified cDNA fragments. Thus, if the optimum annealing temperature is 42° C. a shift of the annealing temperature up or down by 2° resulted in the appearance of a substantial background (i.e., additional bands) or to disappearance of some bands [7]. Second, according to the data of the authors of [7] when parallel experiments were carried out, about 95% of bands proved to be reproducible [6]. Thus, the level of nonreproducibility (5%) is comparable to or even exceeds the level of differences between mRNA populations. According to our data, when this approach is used, the number of reproducible differential bands is usually smaller than the number of nonreproducible bands. It is probable that the sensitivity of the approach to the quality of preparations of RNA, primers, annealing time and other parameters may substantially prevent a comparison of results with known data.

SUMMARY OF THE INVENTION

The basis of the invention was the task of supporting the possibility of a direct qualitative and quantitative comparison of the spectra of mRNAs synthesized in different types of cells of the same organism, the possibility of detection of differentially expressed RNAs, including those with a low level of representation, the possibility of correlating these RNAs with known ones, and also the possibility of cloning fragments of such RNAs. The problem is resolved by the fact that the set of messenger RNAs expressed in a cell by means of synthesis of complementary DNA (cDNA) with subsequent fragmentation of the cDNA by frequently cleaving restriction endonucleases (having four- or five-letter recognition sites) and use of the cDNA fragments corresponding to the 3' or 5' ends of the mRNA, is represented in the form of a set of fragments of cDNA of discrete length, no more than one fragment for each species of mRNA, and at least one of the ends of the fragments carries the marker or group necessary for detection. The generated fragments of cDNA originate from the 3' end (adjacent to the poly(A) tail) or 5' end regions of the mRNAs and support representation, depending on the specific embodiment of the invention, of from 90% to essentially 100% of mRNA sequences. For an increase of the sensitivity of the approach and for unambiguous identification of individual fragments the set of cDNA fragments may be divided into several nonintersecting subsets of fragments. The sets or subsets are divided by one- or two-dimensional gel electrophoresis and detection of the marker and comparison of the separation pictures is carried out. In this case the intensity of the signal from each fragment of cDNA varies for mRNA preparations from different cells in proportion to the representation of the sequence corresponding to it in the mRNA pool. If necessary in the detection stage, by means of transfer of the separated fragments to a membrane and sequential hybridization with a set of oligonucleotides, which partially overlap the common end sequence of the fragments, additional analysis of the separation picture is possible. The separated cDNA fragments, after additional operations can be amplified and investigated by means of restriction and hybridization analysis and also sequencing, and can be cloned to a plasmid or phage vector.

Thus, in the proposed invention, in contrast to the approach using arbitrary primers, at least one of the boundaries of the fragments is specified by the position of the restriction site*; in addition, in the proposed approach a set of cDNA fragments that is as representative as possible is created at first and then divided into nonintersecting subsets and then separated with the aid of gel electrophoresis. The use of the reaction of cleavage of DNA by restriction nucleases, which is characterized by high specificity, completeness of cleavage and low sensitivity to variations of temperature conditions, makes it possible to make the approach much more reproducible and, therefore, will make possible a reliable comparison with independently conducted experiments. These characteristics, together with the high resolution of the method, will make it possible to begin the creation of databases of gel coordinates of expressed sequences. The proposed method makes it possible to eliminate the excess of information that is characteristic for the method with arbitrary primers. In addition the presence of one common population of cDNA fragments in the initial stages makes it possible to conduct such operations as frequency equalizations by means of self-hybridization of the population of cDNA fragments [8], which will make it possible to reduce substantially the level of representation of the most frequently encountered mRNA species and will help the isolation of very rare mRNA sequences owing to a reduction of interference from frequently encountered sequences.

BRIEF DESCRIPTION OF THE DRAWINGS

FIGS. 4A and 4B represent hybridization of cloned fragment 1 (a) and fragment 2 (b) with preparations of poly(A)$^+$ RNA from mouse spleen (1) and thymus (2) separated by electrophoresis and transferred to a membrane. The hybridization confirms the specificity of expression that follows from FIG. 3. On the right are plotted marker single-chain DNA fragments and their lengths and nucleotides are indicated.

DETAILED DESCRIPTION OF THE INVENTION

Figure 1:
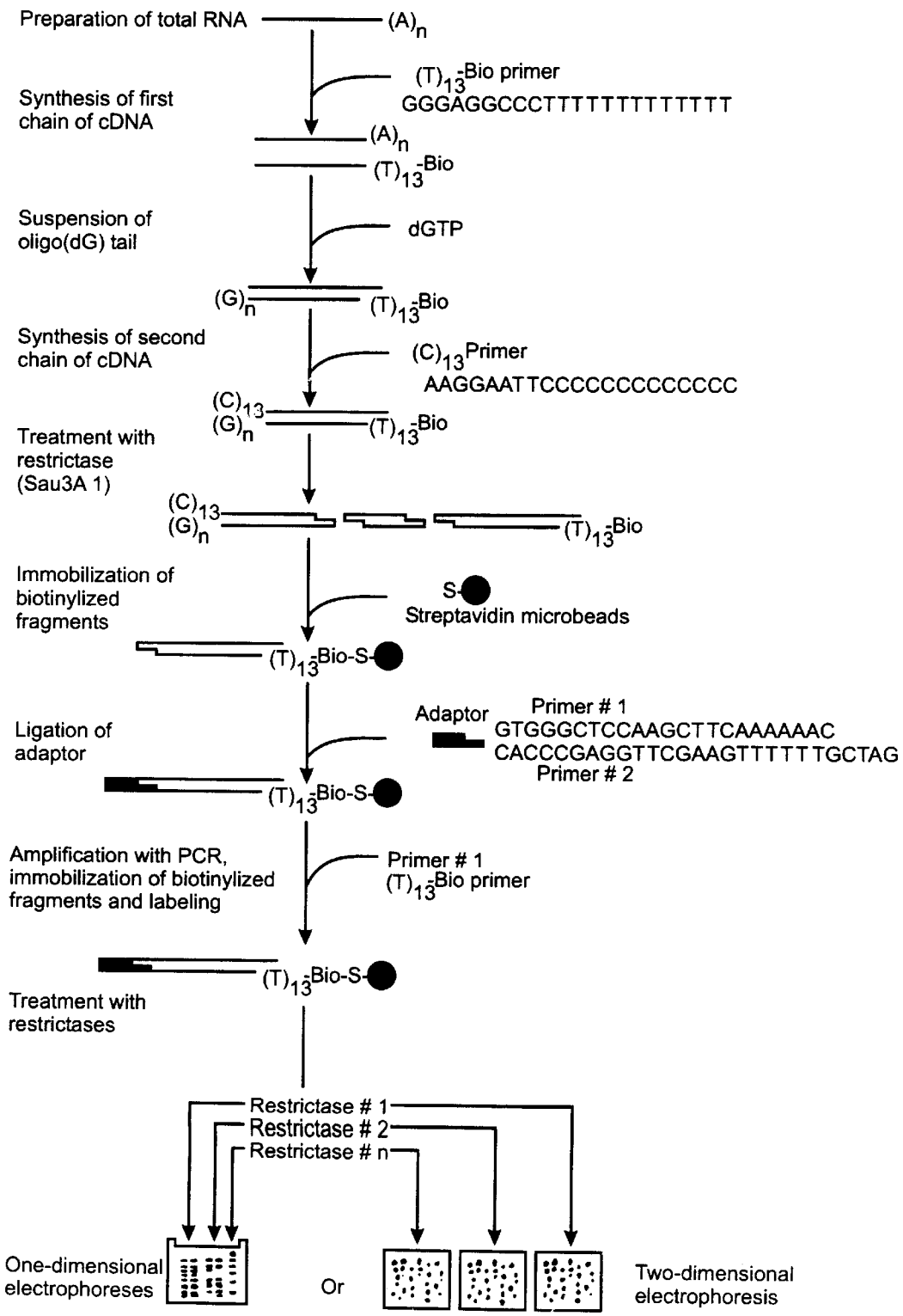
FIG. 1 shows one version of implementing the invention by means of the formation of a set of 3' end labeled fragments of cDNA, dividing it into subsets of fragments with the aid of immobilization on a solid support and sequential treatment with a series of restriction nucleases, and separation of the resulting subsets by electrophoresis.

One variation of the announced method is presented in more detail below.

Synthesis of the first chain of cDNA is accomplished by the enzymatic route with the aid of reverse transcriptase and oligo(dT) primer immobilized on microgranular solid support or of oligo(dT)-containing primer carrying a biotin group at the 5' end. For synthesis of the second chain of cDNA, preliminary suspension of the oligo(dG) tail at the 3' end of the first chain of cDNA with the aid of terminal transferase is carried out. Synthesis of the second chain is carried out with modified DNA polymerase of phage T7 sequenase (United States Biochemicals, USA) using an oligo(dC)-containing primer as primer. Complete hydrolysis of the cDNA with restriction endonuclease. having a four-letter recognition site (for example, Sau3A), rinsing of the released cleavage products and ligation of the adaptor complementary to the cleavage site are carried out. If a biotinylized primer is used for synthesis of the first chain, the cDNA before or after cleavage with restrictase is bonded to a streptavidin-containing solid support (Streptavidin MagneSphere, Promega, USA). The ability of streptavidin to bind the biotin group rapidly and stably is used in this operation. To increase the above material, amplification of the fragments of cDNA is carried out by means of PCR using the primer that is in the adaptor and modified oligo(dT) primer containing the biotin group at the 5' end. After immobilization of the fragments in the streptavidin-containing solid support the free ends are removed by treating with 100 mM NaOH, and then the primer is annealed in the immobilized chains, the label is added to the 3' end of the primer by the chain lengthening reaction with DNA polymerase using radioactive $\alpha$-$^{32}$P DATP or $\alpha$-$^{33}$P DATP, after which unlabeled deoxynucleotide triphosphates are added and complete chains of cDNA are completed. The sequence of primer and segment cDNA annealed with it and also the conditions of the labeling reaction are such that the region labeled is limited to the adaptor sequence. After adding the marker, sequential exhaustive cleavage with 8–10 restrictases is carried out, with restrictases having 6-letter recognition sites being used first, followed by 5-letter and finally 4-letter recognition sites. The released labeled fragments of cDNA after each reaction are collected separately. Separation of the fragments is done with one of the systems for electrophoresis in polyacrylamide or similar gel (Hydrolink, AT Biochem, USA). The system of two-dimensional electrophoresis of DNA, in which separation of the double-chain DNA along the length is carried out in the first reaction, and separation with regard to composition is done in the second direction (more precisely, over the melting profile) with a denaturing gradient [9]. According to literature data, even after transfer to a membrane, which significantly degrades resolution, this kind of system makes it possible to separate at least 625 fragments of DNA on one gel [10]. To all appearances the upper limit of resolution is 1 to 1.5 thousand DNA fragments. If the population of cDNA fragments is divided into 8–12 nonintersecting sets, one can separate up to 10–15 thousand fragments, i.e., essentially all mRNAs expressed in cells of a single type. The signal from the separated fragments is detected by means of autoradiography on x-ray film. The pictures obtained from preparations of RNA from different types of cells are compared with each other, the correspondence between individual fragments of cDNA from different cells is established from the position in one- or two-dimensional electrophoresis and fragments giving a differential signal are identified.

In order to ascertain the sequence of known sequences to which one or another spot on the two-dimensional electrophoreogram may correspond, one first, based on cloned sequences of mRNAs in the data bank, determines which sequences may give fragments of the corresponding link and then,-by using the algorithm for prediction of mobilities of fragments of DNA in a denaturing gradient [11], one can choose from these sequences the one whose melting profile most accurately corresponds to the position occupied by the fragment in the second direction.

Figure 2:
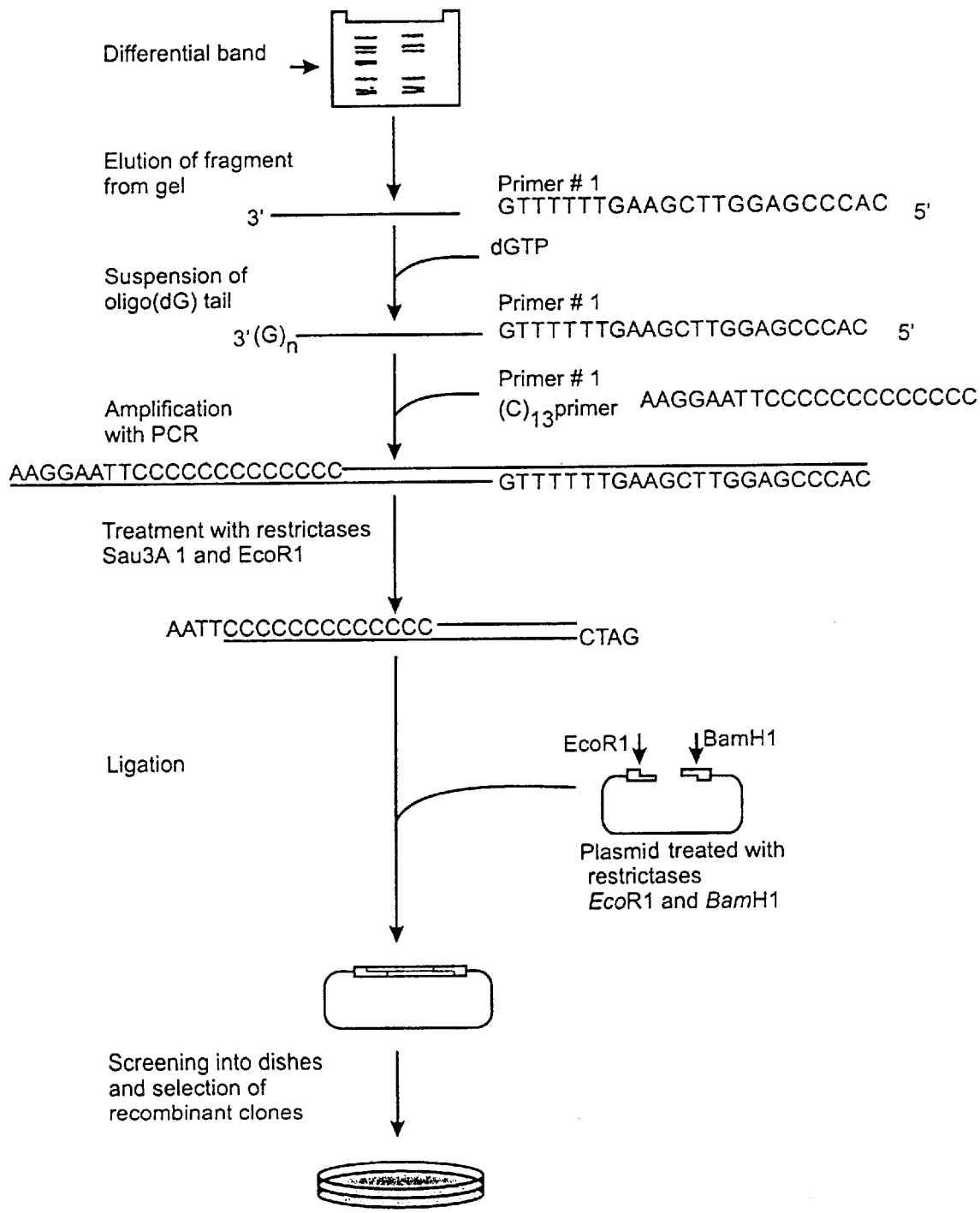
FIG. 2 shows a scheme of amplification and cloning of cDNA fragments obtained and separated in gel with the aid of the method shown in FIG. 1.

In order to obtain the needed fragment in a quantity sufficient for analysis and cloning, the fragment is eluted from the gel, the oligo(dG) tail is suspended with the aid of terminal taansferase, and then amplified by means of PCR using adaptor primer and oligo(dC) (FIG. 2). The identical nature of the fragment of the known sequence can be verified by means of restriction analysis or by determining the nucleotide sequence directly in the amplified fragment. In addition, the amplified fragment may be easily cloned to the plasmid or phage vector.

Our commuter analysis of 659 cloned sequences of mouse mRNA having a sequestered region belonging to the poly(A) tail showed that when the restriction endonuclease Sau3A (recognition site: GATC) was used for cleavage of the cDNA 93% of all mRNAs will be cleaved by the enzyme and, therefore, will participate in the analysis. The fraction of sequences of mRNAs participating in the analysis can be increased to 99%–99.5%, if cleavage is done with a second restrictase having a different recognition site of those sequences of cDNA that were not cleaved by the first restrictase. The computer analysis also shows that second cleavage of immobilized fragments of cDNA with a set of restriction endonucleases can reach the overwhelming majority of fragments (96% if ten four-letter restrictases are used). Thus, from 90 to 96% of all mRNA sequences of the cell will be represented in the form of discrete fragments of cDNAs and will participate in the analysis period.

The proposed method has high sensitivity. Using only 1 $\mu$g of cDNA fragments for labeling it is easy to obtain inclusion to $10^8$ count/min. This level of labeling makes it possible to detect MRNA sequences that make up from 0.001% to 0.0001% of the mRNAs of the cell.

Besides the variation described above, there are also other variations of the invention. Synthesis of the second chain of cDNA can be accomplished by other known methods by using as primers for synthesis the chain of RNA in hybrid cDNA-RNA that has been cleaved with the aid of RNAse H or by using self-priming of the first cDNA chain after hydrolysis of the RNA chain [12]. The most important modification is the use of the alternative method of dividing the set of 3' end fragments of cDNA into nonintersecting subsets of fragments by means of amplification with the aid of 12 different pairs of primers, which include a) four versions of a modified adaptor primer, which includes an adaptor end sequence that is common for all fragments of cDNA and that each contains one additional base at the 3' end; b) three versions of oligo(dT)-containing primer that contains one additional base at the 3' end. In this case one employs the property of Taq DNA polymerase to extend only those primers that contain a completely paired 3' end base [13]. In this version it is not necessary to carry out second cleavage with the set of restrictases and, therefore, the share of mRNA sequences that participate in the analysis can essentially reach 100%.

Figure 6:
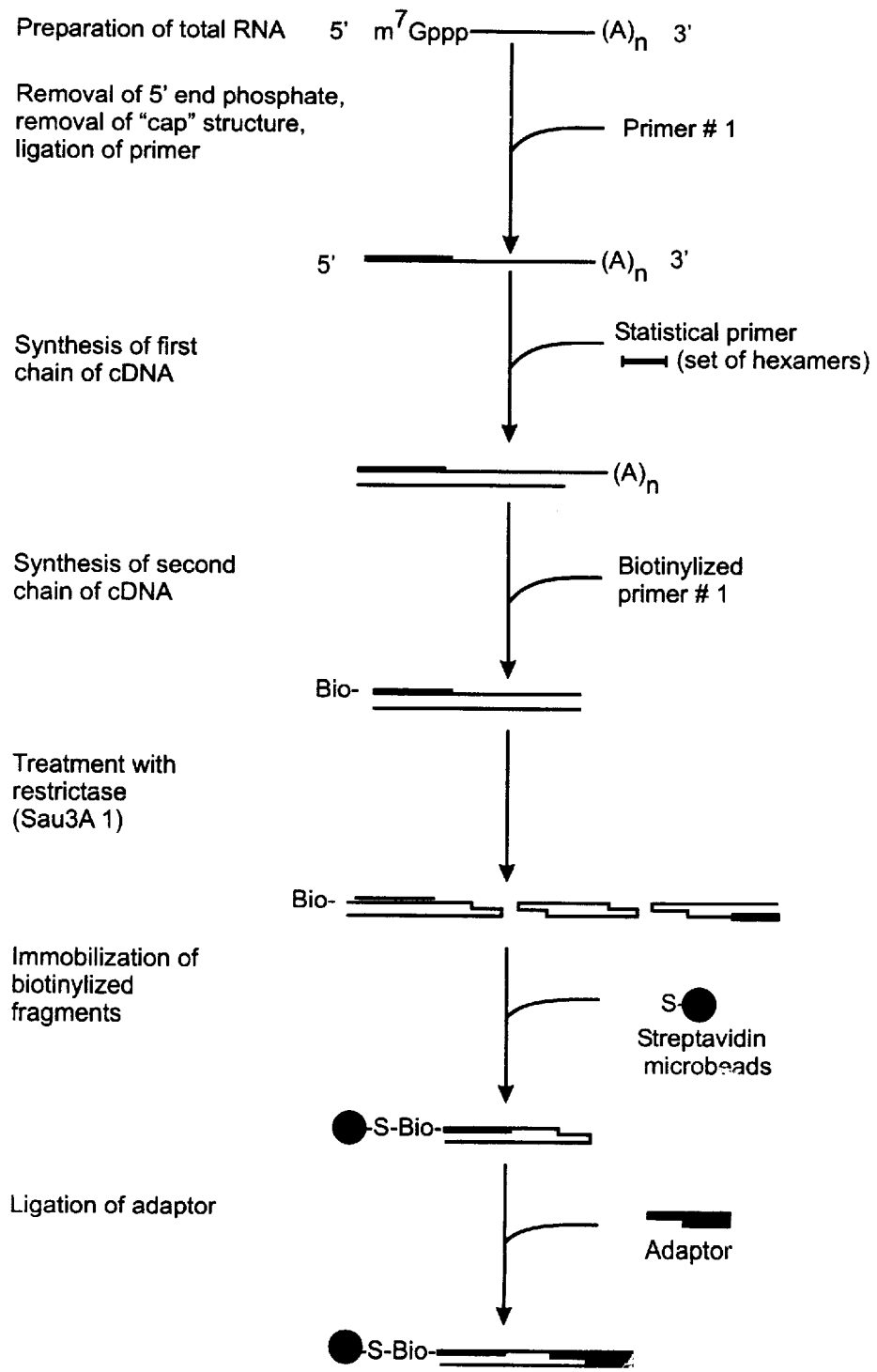
FIG. 6 shows a method of creating a set of 5' end fragments of cDNA.

One further important version of the approach is creation of a set of fragments of cDNAs corresponding to the 5' end of the mRNAs (FIG. 6). For this one uses specific labeling of the 5' end of the mRNAs with an oligonucleotide primer (primer 1) in accordance with the procedure of [14]. After this, one synthesizes the first chain with the aid of a set of random hexamer primers, synthesizes the second chain with the aid of primer 1 containing a biotin group at the 5' end, immobilizes the cDNAs in streptavidin microgranules, followed by hydrolysis of the cDNAs with restrictase, ligation of the adaptor and other procedures, as indicated above. Dividing the set of 5' end fragments of cDNAs into subsets is accomplished either by immobilization of the labeled fragments and sequences by treatment with restrictases or with the aid of separate reactions of amplifications with end primers that contain an additional base at the 3' end, as indicated above.

Besides two-dimensional electrophoresis using a denaturing gradient in the second direction, it is also possible to use systems of two-dimensional electrophoresis that use in the second direction separation of single-chain DNA under nondenaturing conditions owing its conformational polymorphism [15] or cleavage of DNA after the first direction by frequently cleaving restrictases [16] and separation by length in the second direction.

Besides the use of radioactive $^{32}P$ or $^{33}P$ markers with subsequent autoradiography for detection, a nonradioactive variation of detection may also be accomplished; in this version labeling of the fragments of cDNA is done with biotin groups or other chemical groups that after transfer of the fragments to the membrane and immobilization are detected with one of the commercial systems of nonradioactive detection using chemiluminescence.

Detection of the separated unlabeled elements of cDNA can be done by transfer of fragments to a membrane and hybridization with a labeled adaptor primer. In this case, after hybridization with the adaptor primers that contain additional based at the 3' end, selected visualization of the subsets of fragments separated in the given gel is possible.
Information Confirming the Possibility of Implementation of the Invention To support the possibility of identification and cloning of differentially expressed mRNAs, the experiments presented in the following example were carried out.

EXAMPLE

Identification and cloning of mRNAs differentially expressed in mouse thymus and spleen.

Preparations of total RNA are extracted from mouse thymus and spleen in parallel using extraction with acid phenol [17]. Synthesis of the first cDNA chain was accomplished under the following conditions: 37° C., 60 min, reaction volume 20 µL, 5 µg total RNA, 200 U reverse transcriptase Superscript (Gibco-BRL, USA), 10 pmol (T)-primer, biotinylized at the 5' end (sequence 5'-biotin GGGAGGCCC(T)$_{13}$) (SEQ ID NO:1), 30 U RNAse inhibitor from human placenta, dATP, dGTP, dCTP, dTTP (1 mM each), 1x buffer of reverse transcriptase in accordance with manufacturer's recommendations make up the reaction mixture. Removal of the primer is done with the aid of reprecipitation using cetyltrimethylammonium bromide [18], after which additional purification is carried out on a Wizard column (Promega, USA) according to manufacturer's recommendations. The purified preparation is precipitated with 3 volumes of ethanol using 2 µg glycogen (Boehringer-Mannheim, Germany) as carrier.

Suspension of the oligo(dG) tail is done under the following conditions: 37° C., 20 min, reaction volume 20 µL, with the reaction mixture containing hybrid mRNA-first chain of cDNA, 20 U terminal transferase (Gibco-BRL, USA), 0.02 mM dGTP, 1x buffer of terminal transferase in accordance with manufacturer's recommendations. Synthesis of the second chain of cDNA is done under the following conditions: denaturation 98° C., 1.5 min, annealing 60° C., 2 min, elongation 72° C., 20 min, reaction volume 25 µL, reaction mixture contains: hybrid mRNA-cDNA, 10 pmol (C)-primer (sequence 5'-AAGG ATT(C)$_{13}$) (SEQ ID NO:2), dATP, dGTP, dCTP, dTTP (0.1 mM each), 1.5 U DNA polymerase Bio-Taq (Biomaster, Russia), 1x buffer of Bio-Taq in accordance with manufacturer's recommendations. Cleavage of cDNA by restriction endonuclease is done under the following conditions: 37° C., 60 min, reaction volume 20 µL, 4 U restriction endonuclease Sau3A (New England Biolabs, USA), 1x buffer of enzyme (according to manufacturer's recommendations). After hydrolysis the reaction is stopped by the addition of EDTA to 20 mM and the 3' end fragments of cDNA are immobilized on Streptavidin microbeads (Promega, USA) in accordance with manufacturer's recommendation. The adaptor is added:

1. 5'-GATCGTTTTTTGAAGCTTGGAGCCCAC-3' (SEQ ID NO:3)
2. 3'-CAAAAAACTTCGAACCTCGGGTG-5'(SEQ ID NO:4)

and ligated at 12° C. overnight. Reamplification of the cDNA fragments with the aid of PCR is done using Bio-(T$_{13}$) primer and primer 1 under the following conditions: denaturation 95° C., 1.2 min. annealing 55° C., 1.5 min, elongation 72° C., 3 min* reaction volume 100 µL, reaction mixtures contains: 30 pmol Bio-(T) primer, 30 pmol primer 1, 2.5 U DNA polymerase Bio-Taq; the mixture of deoxynucleotide triphosphates, 0.1 mM each, 1x buffer of Bio-Taq. After 15 PCR cycles the fragments are immobilized an Streptavidin microbeads (Promega, USA), then the free chain is removed by treatment with 100 mM NaOH for 10 min, rinsing with a buffer of composition: 40 mM Tris-Cl, pH 7.0, 20 m McgCl$_2$, 50 [?] NaCl, primer 3 (5'-GGGCTCCAAGCTTC) (SEQ ID NO:5) is annealed, radioactive α-$^{32}$P dATP is added and the marker is added over 5 min using modified DNA polymerase of phage T7 Sequenase (United States Biochemicals, USA), after which the mixture of dNTP is added (to 0.2 mM each) and complete chains are finished. Cleavage of the fragments is done successively with restriction endonucleases EcoRV, PstI, MspI, Hin PI (New England Biolabs, USA). After each endonuclease treatment the fragments are collected, denatured and applied to sequestering polyacrylamide gel (5% acrylamide, 0.25% methylene-bisacrylamide, 7M urea, 1x TBE buffer). Separation of the fragments is done under standard conditions after which the gel is fixed in 10% acetic acid for 30 min, dried and autoradiographed. The sequences of mRNAs that are differentially expressed in thymus and spleen are identified by means of a direct comparison of the sets of bands of cDNA obtained from thymus and spleen and separated in adjacent tracks. For cloning of the differentially expressed sequences the corresponding bands of gel are cut apart and the fragments are eluted by incubation in 150 mM NaCl, 50 mM Tris-Cl, pH 8.0, 10 mM EDTA overnight. Then precipitation of the fragments is carried out with three volumes of 96% ethanol using glycogen as carrier. The oligo(dG) tail is suspended at the 3' end of the fragment using terminal transferase, as described above, and the fragment that has been processed in this way is amplified by means of PCR using (C) primer and primer 1.

The amplified fragment is purified with the aid of electrophoresis in agarose gel, transferred to low melting agarose and recovered in pure form with the aid of phenol extraction [19]. For cloning of the fragments they are treated with restrictase Sau3A and EcoRI and ligated to plasmid vector pUC18 cleaved by restrictase BamHI and EcoRI, after which they transform competent bacteria. The presence of recombinant clones is verified with the aid of amplification of insertions using PCR. Verification of the specificity of the cloned fragments is done by means of hybridization of $^{32}$P-labeled insertions from clones with blots of amplified cDNA and poly(A)$^+$ RNA from the corresponding organs.

Figure 3:
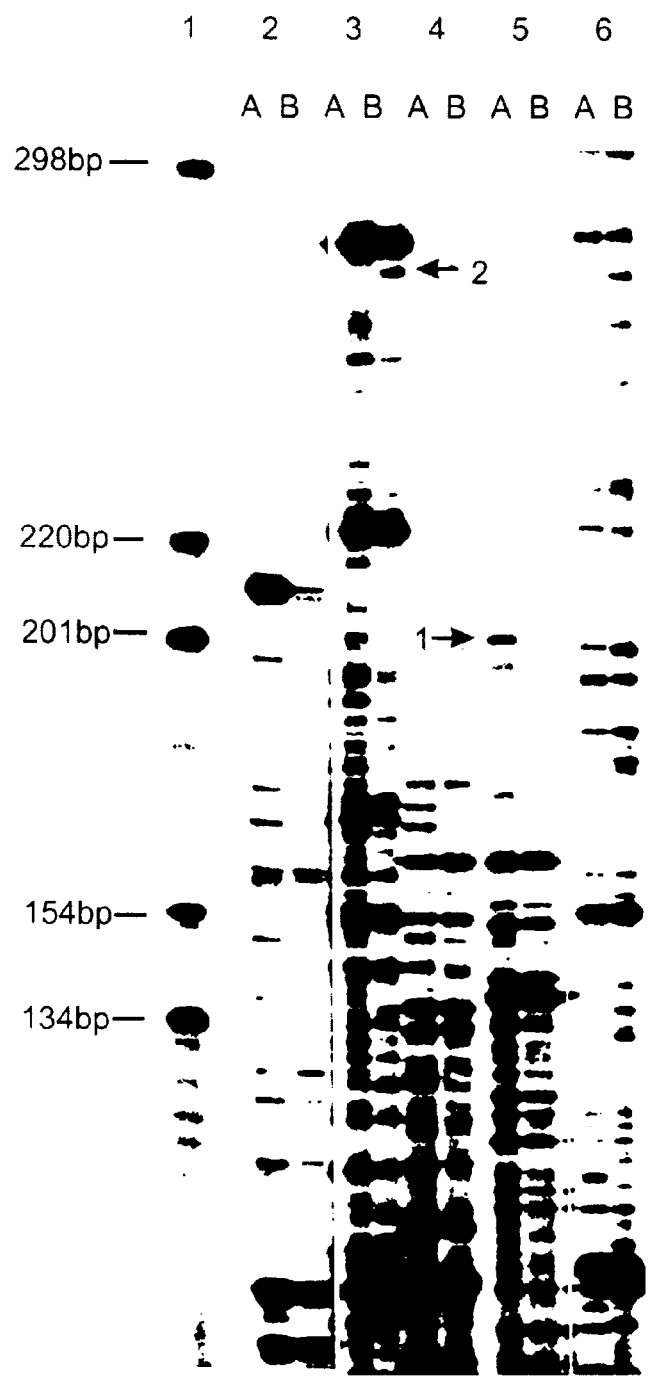
FIG. 3 shows a representation of separation in denaturing polyacrylamide gel electrophoresis of $^{32}$P-labeled fragments of cDNA from preparations of RNA of mouse thymus (a) and mouse spleen (b) obtained with the aid of the method presented in FIG. 1. The first cleavage was done with the enzymes Sau3A (2–5) and BamHI (6), the second with the enzymes EcoRV (2), PstI (3, 6), MspI (4) and Hin PI (5). Microfragments of DNA are plotted on the left (1) and their lengths in nucleotides are indicated.
Figure 5:
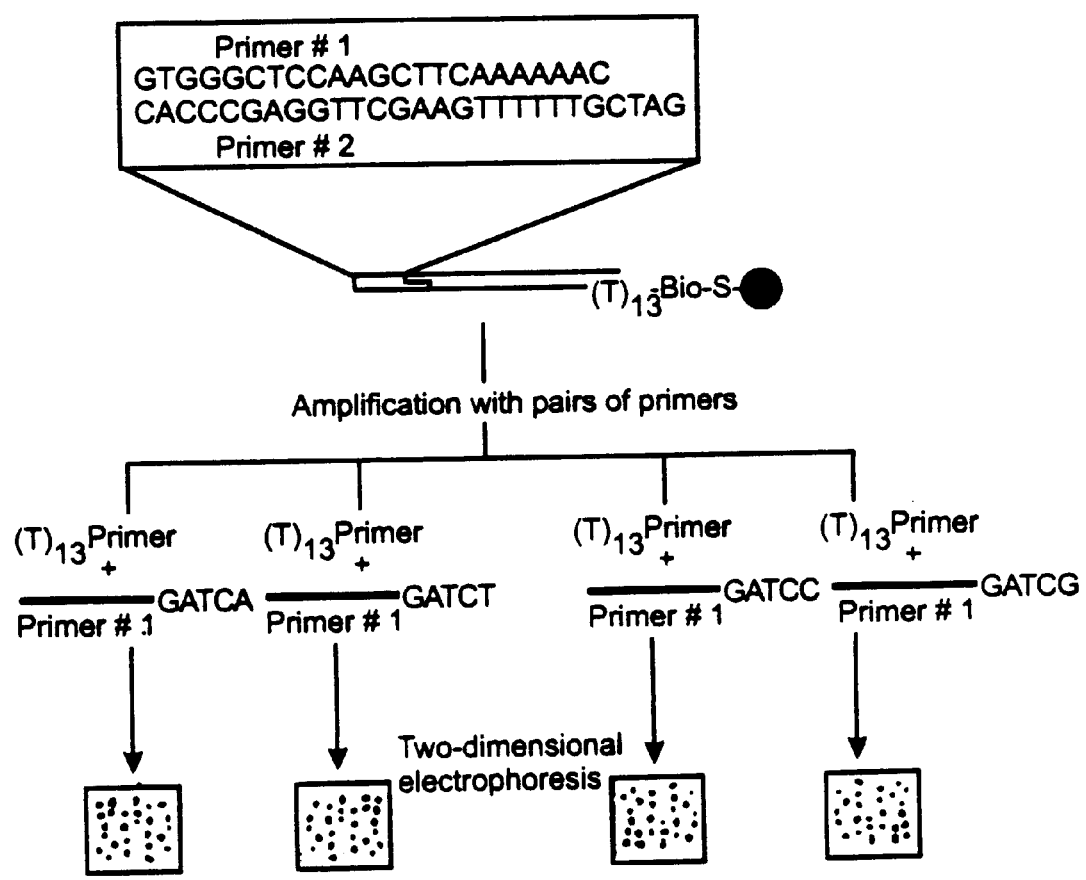
FIG. 5 shows an alternative method of dividing the set of 3' end fragments of cDNA obtained by the method shown in FIG. 1 into four subsets by means of amplification of the set of fragments by a polymerase chain reaction with adaptor primers that contain a supplemental base at the 3' end beyond the limits of the part that is common for all fragments.

The data in FIG. 3 show that this method leads to the formation of a multitude of labeled discrete fragments of cDNAs which can be separated in gel electrophoresis, and in comparing the pictures of the separation of cDNAs from two different organs one can identify differential bands. The fragments corresponding to the differential bands can be amplified and cloned by the method indicated in FIG. 2. The data given in FIG. 4 show that the cloned fragments of cDNAs are indeed mRNAs differentially expressed in two organs.

REFERENCES

1. Sargent, T. D. Isolation of differentially expressed genes. Methods in Enzymol. (1987) 152, 423–432.

2. PCT/G 89/00460 (1989)

3. Welsh, J., Chada, K., Dalal, S. S., Cheng, R., Ralph, D., McClelland, M. Arbitrarily primed PCR fingerprinting of RNA. Nucl. Acids Res. (1929) 20, 4965–4970.

4. Ralph, D., McClelland, M., Welsh, J. RNA fingerprinting using arbitrarily primed PCR identifies differentially regulated RNAs in mink lug (Mv1Lu) cells growth arrested by transforming growth factor-beta 1. Proc. Natl. Acad. Sci. USA (1993) 90, 10710–10714.

5. Liang, P., Pardee, A. B. Differential display of eukaryotic messenger RNA by me of the polymerase chain reaction. Science (1992) 257, 967–971.

6. Liang, P., Averboukh. L., Pardee, A. B. Distribution and clonging of eukaryotic mRNAs by means of differential display; refinements and optimization. Nucl. Acids Res. (1993) 21, 7. Bauer, D., Muller, H., Reich, J., Riedel, H., Ahrenkiel, V., Warthoe, P., Strauss, M. Identification of differentially expressed mRNA species by an improved display technique (DDRT-PCR). Nucl. Acids Res. (1993) 21, 4272–4280.

8. Sasaki, Y. F., Iwaskaki, T., Kobayashi, H., Tsuji, S., Ayusawa, D., Oishi, M. Construction of an equalized cDNA library from human brain by semi-solid self-hybridization system. DNA Research (1994) 1, 91–96.

9. Fischer, S. G., Lerman, L. S. Length-independent separation of DNA restriction fragments in two-dimensional gel-electreophoresis. Cell (1979) 16, 191–200.

10. Uitterlinden, A. G., Slagboom, P., Knock, D. I., Vijg, J. Two-dimensional DNA fingerprinting of human individuals, Proc. Natl. Acad. Sci. USA (1989) 86, 2742–2746.

11. Lerman, L. S., Silverstein, K. Computational simulation of DNA melting and its application to denaturing gradient gel electrophoresis. Methods in Enzymol. (1987) 155, 482–501.

12 Kimmel, A. R., Berger, S. L. Preparation of cDNA and the generation of cDNA libraries: Overview. Methods in Enzymol. (1987) 152, 307–316.

13. Newton C. R., Grahm, A., Heptinstall, L. E., Powell, S. J., Summers, C., Kalsheker, N., Smith, J. C., Markham, A. F. Analysis of any point mutation in DNA. The amplification refractory mutation system (ARMS). Nucl. Acids Res. (1989) 17, 2503–2516.

14. Maruyama, K., Sugano, S. Oligo-capping: a simple method to replace the cap structure of eukaryotic mRNAs with oligoribonucleotides. Gene (1994) 138, 171–174.

15. Orita, M., Iwahana, H., Kanazawa, H., Kayashi, K., Sekiya T. Detection of polymorphism of human DNA by gel electrophoresis as single-strand conformation polymorphisms. Proc. Natl. Acad. Sci. USA (1989) 86, 2766–2770.

16. Hatada, I., Hayashizaki, Y., Hirotsune, S., Komatsubara, H., Mukai, T. A genomic scanning method for higher organisms using restriction sites as landmarks. Proc. Natl. Acad. Sci. USA (1991) 88, 9523–9527.

17. Chomczynski, P., Sacchi, M. Single-step method of RNA isolation by acid guanidinium thiocyanate-phenol-chloroform extraction. Anal. Biochem. (1987) 162. 156–159.

18. Belyavsky, A. V., Vnogradova, T. V., Rajewsky, K. PCR-based cDNA library construction: General cDNA libraries at the level of a few cells. Nucl. Acids Res. (1989) 17, 2919–2932.

19. Sambrook, J., Fritsch, E. F., Maniatis, T., eds. Molecular Cloning. A laboratory manual. Second ed. (1989) Cold Spring Harbor Laboratory Press, New York.

Key: 1 Preparation of total RNA

2 Removal of 5' end phosphate, removal of "cap"structure, ligation of primer

3 Synthesis of first chain of cDNA

4 Synthesis of second chain of cDNA

5 Treatment with restrictase (Sau3A 1)

6 Immobilization of biotinylized fragments

7 Ligation of adaptor

8 Primer #1

9 Statistical primer (set of hexamers)

10 Biotinylized primer #1

11 Streptavidin microbeads

12 Adaptor

We claim:

1. A method of identifying mRNA species in a sample, comprising the step of assessing amounts of separated cDNA fragments corresponding to said mRNA species;
   wherein said cDNA fragments have been separated by a method comprising the steps of
   (a) cleaving cDNA corresponding to said mRNA species with at least one restriction endonuclease to generate cDNA fragments;
   (b) amplifying, with one or more primers, one or more cDNA fragments directly resulting from the restriction endonuclease cleaving; and
   (c) separating amplified cDNA fragments corresponding to said mRNA species.

2. A method of identifying mRNA species in a sample according to claim 1, wherein the amplified cDNA of step (b) is further cleaved by at least one restriction endonuclease.

3. A method of detecting signals from a set of cDNA fragments corresponding to the mRNA species in a sample, comprising the steps of:
   (a) cleaving cDNA corresponding to the mRNA species with at least one restriction endonuclease to generate a set of cDNA fragments;
   (b) amplifying, with one or more primers, cDNA fragments in said set;
   (c) separating said amplified cDNA fragments; and
   (d) detecting signals from said separated cDNA fragments.

4. A method of comparing mRNA species that are differentially expressed between two or more samples, comprising the steps of:
   detecting signals from sets of cDNA fragments, wherein each set corresponds to the mRNA species in a sample according to the method of claim 3; and
   comparing said signals from separated cDNA fragments.

5. The method according to any one of claims 1–4, wherein the separating of step (c) comprises electrophoresis.

6. The method according to claim 5, wherein the electrophoresis is two-dimensional gel electrophoresis.

7. The method according to any one of claims 1–4, wherein said cDNA fragments correspond to the 3' end region or the 5' end region of the mRNAs in the mRNA samples.

8. The method of claim 7, wherein the cDNA fragments correspond to the 3' end region of mRNAs in the mRNA samples.

9. The method of claim 7, wherein the cDNA fragments correspond to the 5' end region of mRNAs in the mRNA samples.

10. The method according to any one of claims 1–4, wherein the cDNA fragments are divided into subsets.

11. The method according to any one of claims 1–4, wherein the cleaving of step (a) divides the cDNA fragments into subsets.

12. The method according to claim 11, wherein the subsets are non-intersecting.

13. The method according to any one of claims 1–4, wherein the amplifying of step (b) includes the ligation of an adaptor to the cDNA fragments.

14. The method of claim 13, wherein the adaptor is complementary to the restriction endonuclease cleavage site.

15. The method according to any one of claims 1–4, further comprising the step of enriching the degree of representation of different sequences within the sample by removing highly represented sequences.

16. The method according to any one of claims 1–4, wherein the separated cDNA fragments are sequenced.

17. The method according to any one of claims 1–4, wherein the cleaved cDNA is double stranded.

18. The method according to claim 4, wherein mRNA species that are differentially expressed are those whose concentration in the cellular mRNA pool differs in two or more types of cells or changes in dependence on the functional state of the cells.

19. The method according to any one of claims 1–4, wherein the cleaving of step (a) is performed with two restriction endonucleases.

20. The method according to claim 19, wherein the restriction endonucleases recognize a six base pair site.

21. The method according to any one of claims 1–4, wherein the cDNA fragments comprise a detectable label.

22. The method of claim 21, wherein the detectable label is selected from the group consisting of a radioactive label, a chemical group and a specific sequence of nucleotides.

23. The method of claim 21, wherein the detectable label comprises a nucleotide labeled with $^{32}P$ or $^{33}P$.

24. The method of claim 21, wherein the detectable label permits non-radioactive detection of said cDNA fragments.

25. The method of claim 24, wherein said non-radioactive detection is by chemiluminescent detection.

26. The method according to any one of claims 1–4, wherein said cDNA fragments represent from 90% to essentially 100% of the mRNA sequences in the sample.

27. The method according to claim 26, wherein said cDNA fragments represent from 90% to 96% of the mRNA sequences in the sample.

28. The method according to claim 26, wherein said cDNA fragments represent from 99% to 99.5% of the mRNA sequences in the sample.

29. The method of any one of claims 1–4, wherein the restriction endonuclease recognizes a 4, 5 or 6 base pair site.

* * * * *